United States Patent [19]

Adams

[11] Patent Number: 5,966,711
[45] Date of Patent: Oct. 12, 1999

[54] AUTONOMOUS INTELLIGENT AGENTS FOR THE ANNOTATION OF GENOMIC DATABASES

[75] Inventor: R. Mark Adams, Natick, Mass.

[73] Assignee: Alpha Gene, Inc., Woburn, Mass.

[21] Appl. No.: 08/837,963

[22] Filed: Apr. 15, 1997

[51] Int. Cl.$^6$ .................................................. G06F 17/30
[52] U.S. Cl. ......................................... 707/104; 707/200
[58] Field of Search ................................ 707/104, 10, 6, 707/200

[56] References Cited

U.S. PATENT DOCUMENTS

| | | | |
|---|---|---|---|
| 5,379,420 | 1/1995 | Ullner | 395/600 |
| 5,404,295 | 4/1995 | Katz et al. | 364/419.19 |
| 5,546,577 | 8/1996 | Marlin et al. | 395/600 |

FOREIGN PATENT DOCUMENTS

| | | | |
|---|---|---|---|
| 0646883 A1 | 4/1995 | European Pat. Off. | G06F 17/30 |
| 0747841A1 | 12/1996 | European Pat. Off. | |
| 0747842A1 | 12/1996 | European Pat. Off. | |
| 95/20681 | 8/1995 | WIPO . | |
| 96/23078 | 8/1996 | WIPO . | |
| 96/23265 | 8/1996 | WIPO . | |
| 96/38589 | 12/1996 | WIPO . | |

OTHER PUBLICATIONS

Saake, et al., "From Object Specification towards Agent Design," ESPRIT Basic Research Working Group No. 8319 ModleAge (A Common Formal Model of Cooperating Intelligent Agents), pp. 329–340, no date given.

Fukuoka, et al., "Novel strategy for synthesis of full–length double–stranded cDNA transcripts without dC–dG tails," *Nucleic Acids Research*, 19(24):6961–6962 (1991 Oxford University Press).

Keele, et al., "A Conceptual Database Model for Genomic Research," *J. Computational Biology*, 1(1):65–76 (1994).

Owen, David J., "Library Instruction of Genome Informatics: An Introductory Library Class for Retrieving Information from Molecular Genetics Databases," *Science & Technology Libraries*, 15(3):3–15 (1995).

Weiss, et al., "Adaption and Learning in Multi–Agent Systems," IJCAI '95 Workshop, Montréal, Canada, Aug. 21, 1995 Proceedings, pp. 1–21.

Keen, et al., "The Genome Sequence DataBase (GSDB): meeting the challenge of genomic sequencing," *Nucleic Acids Research*, 24(1):13–16 (1996).

Smith, Randall F., "Perspectives: Sequence Data Base Searching in the Era of Large–scale Genomic Sequencing," *Cold Spring Harbor Laboratory Press*, ISSN 1054–9803/96, 6:653–660.

Drews, J., "Genomic Sciences and the Medicine of Tomorrow," *Nature Biotechnology*, 14:1516 and 1518, Nov. 1996.

Ferguson, Innes A., "A Brief History of Agents." *In Bots & Other Internet Beasties*, Joseph Williams, eds. (Indianapolis: Sams Net Publishing ISBN 1–57521–016–9), pp. 467–491 (1996).

Markowitz, V., et al., "Data Management Tools for Genomic Applications: A Progress Report," *Database and Expert Systems Applications, 4$^{th}$ International Conference, DEXA '93 Proceedings*, Proceedings of 4$^{th}$ International Conference on Database and Expert Systems Applications, Prague, Czechoslovakia, Sep. 6–8, 1993, pp. 529–540, XP002080066.

Waldo, P., et al., "An Efficient Delivery of Historical Information for The Mendelian Inheritance in Man Database," *Nineteenth Annual Symposium on Computer Applications in Medical Care. Toward Cost–Effective Clinical Computing*, Proceedings of Nineteenth Annual Symposium on Computer Applications in Medical Care, New Orleans, LA, Oct. 28–Nov. 1, 199, pp. 127–131, XP002080067.

*Primary Examiner*—Jack M. Choules
*Attorney, Agent, or Firm*—Hamilton, Brooks, Smith & Reynolds, P.C.

[57] ABSTRACT

A genomic database system that makes use of autonomous agents for providing access to the database. The autonomous agents, which are preferably implemented in a multitasking environment, each seek target data to be processed and then call a program to process the target data. The results of the program are then placed in the database. The autonomous agent model permits the sequence data and processing programs to be changed without the need to be concerned with data synchronization or heterogeneity. The agents may be implemented as object oriented programs that permit the extraction of generic software code in an agent code base. The agents may implement annotation functions, analysis algorithms, or may control the assembly of gene sequences.

42 Claims, 7 Drawing Sheets

AUTONOMOUS INTELLIGENT AGENTS FOR THE ANNOTATION OF GENOMIC DATABASES

BACKGROUND OF THE INVENTION

Historically, the analysis of genetic information has been carried out using chemical laboratory methods. While such chemical methods can provide adequate information for a limited number of gene sequences, computer-based research tools are increasingly being used for a variety of purposes related to genetic research. These computer-based tools include both hardware and software that perform high speed algorithms and other processes using gene sequence information stored as computer data.

These computerized tools typically include database programs of various types. In the conventional genomic database system a monolithic master program directs a series of algorithms to be performed. Such algorithms may include simple comparisons, such as to determine if a particular gene sequence has been previously identified, or may include more sophisticated mathematical analysis, such as those used to determine if a gene sequence is likely to exhibit certain characteristics. The algorithms may be run on either a database of existing full length sequences or on sequence segments prior to their entry into the database. Furthermore, researchers may wish to record annotations concerning the sequences as records in the database.

This database-oriented approach is to some degree the result of need to unify the efforts of many different individuals working under many different circumstances. For example, genetic analysis algorithms may be provided by academic, government, or commercial sources. Gene sequence data may originate from in-house laboratory tests, from external commercially available databases, or from privately developed sources.

These hardware and software devices have become powerful tools for the researcher in the field of genetics. In particular, once a comprehensive database of gene sequence information is available, many different algorithms may be run at high speed against all of the known gene sequences. The computer based methods thus provide results much more rapidly then if such analysis were carried out as chemical or laboratory experiments.

However, a number of problems occur when changes must be made to the sequence database or to the algorithms. This is especially the case in a real-time commercial environment, where new genetic sequence information and new algorithms are under continuous research and development.

One such problem occurs when a particular genetic sequence algorithm is replaced by a new version. When this happens, the old result records must be updated by running the new version of each algorithm against each of the genetic sequences. Not only may the process be time consuming, but also the database must typically be kept offline while it is being updated, in order to avoid losing track of which sequence records have yet to be updated.

Other problems exist if the database is not static. In particular, the addition of new gene sequence information to the database must be routinely accommodated in commercial environments. New sequence data may become available on a daily or even hourly basis as gene sequences are continuously produced by automated sequencing equipment. When new data is added, each of the existing algorithms must be rerun with the new data.

The problems associated with conventional systems include difficulties other than keeping the database of gene sequences synchronized with the latest versions of the analytical software. If, as in many cases, the software source code is organized to pre-annotate the data before it enters the database, as a first step in a pipeline of analytical algorithms or processes, it can be very difficult to add new tools or update existing ones. For example, if a change is made to the database while gene sequence data are already in the pipeline, then all new result records will reflect the update, but the old result records already in the database will still need to be updated to reflect the changes in the processing.

The solution to this has in the past been typically thought to require halting the processing pipeline long enough to make the required changes, and to then write new software to update the database of old result records to reflect the new process changes. Completing these procedures is a complex task, and is made even more complex by the interruptions in the availability of the database for other purposes. These problems are exacerbated as the number of records increases.

SUMMARY OF THE INVENTION

Ideally, a genomic database system should permit the sequence data and algorithms to be changed without the need to take the database offline or to otherwise be concerned with data synchronization and data heterogeneity issues. It should thus be possible for the database of gene sequences to be updated or added to at a fairly high rate.

At the same time, the set of software tools that are used to analyze or annotate the database should also be permitted to constantly evolve. In fact, it would be ideal if the users could not only change their analysis tools and to have the changes in the tools automatically reflected in the analysis process, but also to have the tools automatically rerun when changes are made to sequence information in the database. The results database should then also be automatically updated.

The present invention accomplishes these objectives by implementing a genomic database and related software code base using an autonomous agent model. In particular, each software tool is implemented as an agent program which autonomously operates on sequence data read from the genomic database.

The software architecture of the agents includes a sensor process, an intelligence process, and an effector process. The sensor process identifies sequence records that need processing. The intelligence process, which is called after the sensor process, runs the software tools on the output of the sensor process to obtain results data. These software tools may implement analytical algorithms or may be of other types such as process control tools. After the intelligence process, the effector process is run. The effector process places the data output by the agent in the form of result records back into the database.

The result records created by the effector process each preferably contain a reference to the gene sequence data and the agent process from which they were created. Typically, the result records also contain a flag to indicate that the particular record has been visited by a particular agent.

The agents may implement various software tools for operating on gene sequence data. These may include functions and algorithms such as expression data retrieval from both external databases and laboratory equipment, mathematical sequence modeling and comparison, and the control of laboratory processes such as sequence finishing. The agents may be used to record annotations concerning the sequence data.

The autonomous agents are implemented as daemon processes in a multitasking operating system environment. The agent processes thus typically wait in a quiescent state most of the time, and are only periodically invoked to look for the presence of sequence records which have not been processed by the agent.

Preferably, each agent performs only one specific role. For example, an agent is typically associated with each particular analytical or process control tool. Because the agents are run as processes in a multitasking environment, each agent may thus run exclusive of the time, mode or the appearance of new sequence records. As a result, complex software infrastructure for process synchronization and database heterogeneity is not needed. Instead, these issues are addressed by using the results record, and in particular, by using a flag that indicates that a particular sequence record has been processed by a particular agent, since the flag is toggled only after the effector process in each agent is completed.

Thus, when a new version of a particular agent is created, the sensor process in the new version of the agent need only seek the target data it is programmed to process, as would normally be the case anyway, and then toggle its associated flag in its results record.

A genomic database system according to the invention therefore permits new sequence records to be added to the database without having to modify or interrupt algorithms which may be already running.

Furthermore, existing agent processes need not be interrupted when new agent processes are added to the system, unless the new agents are expressly programmed to do so.

BRIEF DESCRIPTION OF THE DRAWINGS

The above and further features of the invention include various novel details of construction and combination of components. These novel features will now be more particularly pointed out in the following claims, and their advantages will also become evident as they are described with reference to the accompanying drawings, in which:

DETAILED DESCRIPTION OF PREFERRED EMBODIMENTS

Figure 1:
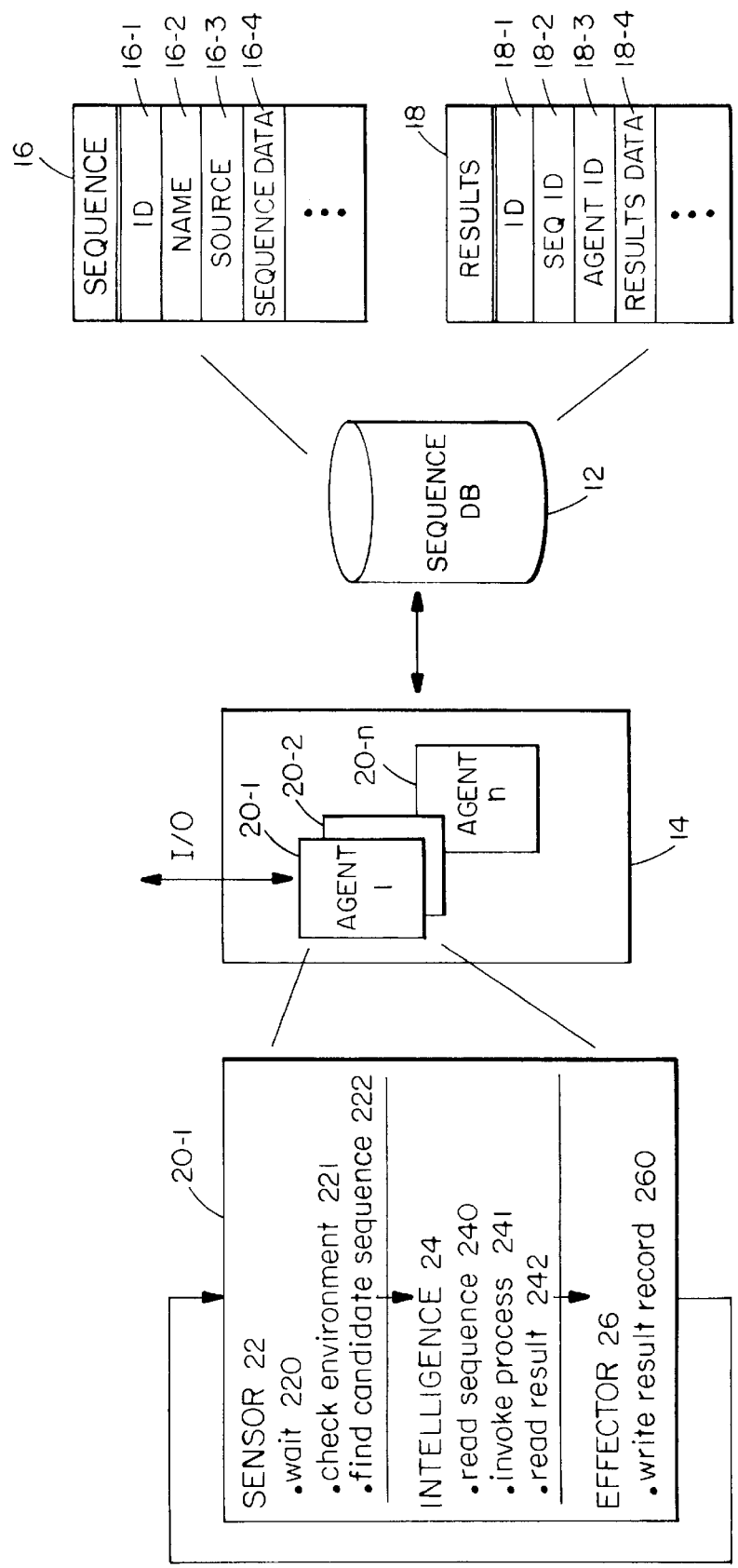
FIG. 1 is a symbolic diagram of an autonomous intelligent agent system for operating with a genomic database according to the invention.

Turning attention now to the drawings, FIG. 1 is a symbolic diagram of a genomic database system 10 which makes use of an autonomous agent processes according to the invention. The system 10 includes a genomic sequence database 12 and a central processing unit 14. The sequence database 12 includes gene sequence and related information in the form of database entries such as a sequence entry 16 and a results entry 18.

The central processing unit 14 has several software entities for performing different tasks. These software entities are referred to herein as agent processes 20-1, 20-2, ..., 20-n (collectively, the agents 20). The central processing unit 14 is of the type that supports a multi-tasking operating system that permits many agent processes 20 to be running simultaneously.

The agents 20, in a manner which will be understood in more detail shortly, obtain access to the sequence database 12 to retrieve data contained in the sequence entries 16. The agents 20 then process the retrieved data and create results entries 18 containing the output of such processing.

Specific agents 20 may be dedicated to a number of different tasks. These tasks may include simple jobs such as locating gene sequence data and adding an annotation to it, or more complex tasks such as comparing known gene sequences against other newly discovered sequences in order to identify their similarities, or may even control processes, such as processes that create full length gene sequences from gene fragments.

The agents 20 are typically autonomous in the sense that they are running all of the time looking for data in the sequence database 12 for which to process. This can be accomplished, for example, by implementing the agents in a multitasking operating system as daemon processes that wait in a quiescent state most of the time, and only periodically activate themselves to search for data.

The agents 20 are also preferably implemented as object oriented programs. This permits each agent to be dedicated to a specific task while at the same time being preferably instantiated as a subclass of an agent core code base, as will also be understood shortly.

Turning attention now to the format of a sequence entry 16 more particularly, each such sequence entry 16 contains a number of records, including an identification record 16-1, a name record 16-2, a source record 16-3, and a sequence record 16-4. The identification record 16-1 contains data such as an index number that provides for unique identification of the particular sequence entry 16. The name record 16-2 contains name information for the gene sequence associated with sequence entry 16. This may include text data items such as a sequence name, a genetic symbol, an organization from which the gene sequence originated, or the tissue sample from which it was taken. The source record 16-3 is used by the system 10 to keep track of where the sequence record 16 originated from, and may include information such as the assembly method, the identification of a well in a laboratory microtiter plate from which the gene sequence sample was taken, the sequence creation date, or other information. Finally, the sequence data records 16-4 contain the actual gene sequence data. The data may typically be in the form of a text record in "ATCG" format, in the case of DNA sequences, or in other formats for other types of genes. The sequence data records 16-4 may actually contain records for several gene sequences of varying lengths. The sequence data records 16-4 may thus include a single gene fragment, a group of fragments, or a complete full length gene sequence.

As explained below, the sequence data records 16-4 may originate from many sources such as laboratory equipment or from other databases, including databases that are external to the system 10, as well as gene sequence data created by the result of running algorithms on other sequence entries 16.

Other entries in the sequence database 12 include results entries 18. Each result entry 18 is associated with a particular sequence record 16 and agent 20; there are typically many different result entries 18 for each sequence entry 16.

Specifically, result entries 18 are created as the agents 20 work on the data contained in the sequence entries 16.

Each result entry 18 includes a number of records such as an identification record 18-1 which uniquely identifies the result entry 18 to the system 10. A sequence identification record 18-2 contains a reference to the sequence entry 16 from which the particular result entry 18 was generated. An agent identification record 18-3 identifies the particular one of the agents 20 which created the result record 18. Finally, at least one result data record 18-4 is included the result entry 18.

In its minimal form, the result data record 18-4 may simply be a flag indicating that the particular agent 20 indicated by the agent record 18-3 has processed the particular sequence entry 16 indicated by the sequence record 18-2. In other instances, the result data record 18-4 contains done more complex data records, such as an annotation output by a particular agent 20 after performing an analysis of the sequence data 16-4 in a particular sequence entry 16.

One feature of the system 10 is that all pieces of data associated with a particular sequence entry 16 are placed in results entries 18. Furthermore, the addition of new sequence entries 16 to the database 12 as well as all other modifications to the database 12 are made through agent processes 20. By so doing, process synchronization and heterogeneity of the database 12 are simple matters to maintain.

To understand this further, consider that only the agents 20 access the data contained in the sequence entries 16, only the agents are permitted to act upon the sequence data, and that only the agents 20 are permitted to record results in the result entries 18.

A specific agent such as agent 20-1 is typically assigned a well-defined unique task. In general the agents 20 each contain program code which can be divided into three categories of functionality, or sub-processes. These include a sensor sub-process 22, an intelligence subprocess 24, and an effector sub-process 26.

As shown in FIG. 1 the sensor sub-process 22 is primarily responsible for identifying sequence entries 16 in need of processing by the particular agent 20-1. The sensor process 22 typically performs a series of steps or states to accomplish this.

A first state includes a wait state 220 in which the agent process 20-1 remains dormant. A check environment state 221 is then entered, in which the agent 20-1 determines the availability of needed resources in the central processing unit 14, and other resources that may be required for carrying out its assigned tasks. If the results of the check environment state 221 are positive, then the sensor process 22 continues to a state 222 to identify a candidate sequence entry 16 which has not yet been processed by the agent 20-1. This may be done by examining results data records 18-4.

Once a candidate sequence entry 16 is found, the agent process 20-1 then proceeds to the intelligence sub-process 24. In this intelligence sub-process 24, a first state 240 reads the sequence data record 16-4 in the sequence entry 16. In a next state 241, other software processes are invoked as necessary to perform the particular task to which the agent 20-1 has been assigned. The invocation of such other processes unique to the agent process 20-1 is carried out in an encapsulated manner such that all relevant outputs therefrom are returned to the intelligence sub-process 24 as results data. Once the particular processes in state 241 are completed, a next state 242 is entered in which the encapsulated results data are read.

Following state 242 the effector sub-process 26 is begun. In this process, the results data provided by the intelligence sub-process 24 are written back into the sequence database 12 as a results entry 18. As the arrow indicates, the agent process 20-1 may then typically return to the performing the sensor process 22 once again.

Figure 2:
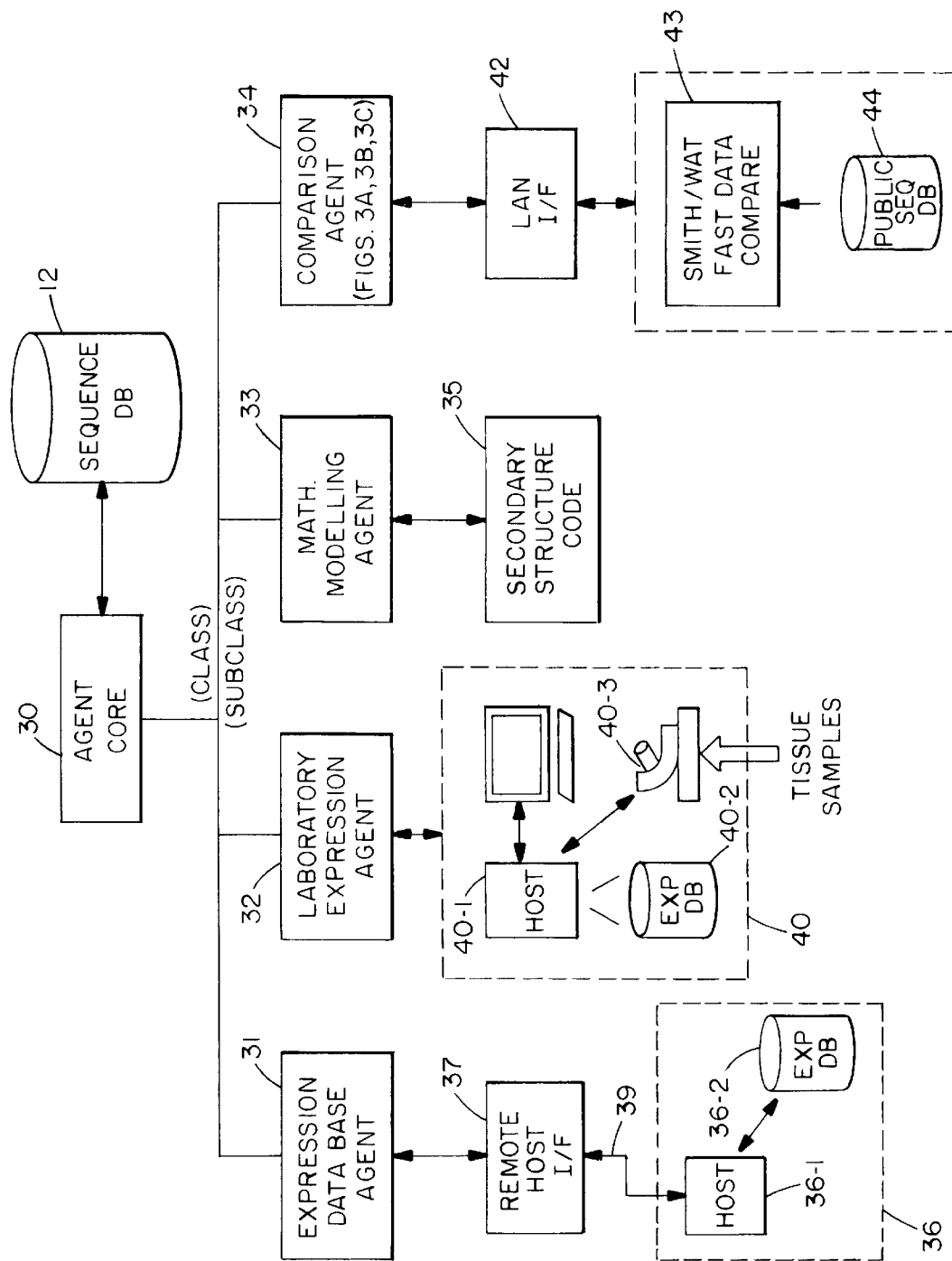
FIG. 2 is a symbolic diagram of various agent subclasses and the manner in which they interact with entities such as hardware devices and software processes both internal and external to the system.

FIG. 2 is a symbolic diagram of the agent core 30 showing several particular types of agents that may be implemented as subclasses of the core 30. The illustrated agents 20 include a gene expression agent 31, a laboratory expression agent 32, a mathematical modeling agent 33, and a comparison agent 34, and a sequence finishing agent 35.

As previously described, the agent core 30 is a software entity that incorporates agent functionality that is global or generic in nature, with the agents 20 being implemented as object oriented programs running in a multitasking operating system environment. Any particular agent such as the agent 20-2 can thus be instantiated as a; subclass of an agent core 30. The agent core 30 can be thought of as a software code base incorporating generic functionality for performing specific tasks common to all agents 20. Such may include code for retrieving sequence entries 16 from the database 12, or for writing the results of such processes in the results entries 18. The agent core 30 thus contains model software processes for controlling control all read and write access to the information in the sequence entries 16 and results entries 18. The agent core 30 may also include code implementing at least the sensor 22, intelligence 24, and effector 26 processes in their most generic state.

Each of the agents shown in FIG. 2 also include specific instantiations of the agent class. That is, each have code in the sensors 22, intelligence 24, and effectors 26 that are specific to their assigned task.

For example, the expression database agent 31 contains code which serves the purpose of obtaining gene sequence data from external sources and writing it as sequence annotation entries in the sequence database 12. The illustrated expression data agent 31 is in particular responsible for obtaining gene expression data located in a remotely located external computer system 36. The external computer system 36 consists of a host processor 36-1 and an associated expression database 36-2. The computer system 36 may, for example, be a publicly or commercially available gene sequence expression database 36-2 that is accessed through a remote host interface software process 37. The remote host interface 37 thus consists of appropriate software for establishing a connection to the remote host 36, presenting a data query instruction, and then receiving the gene sequence data from the expression database 36-2. The interface 39 over which the remote host interface 37 interacts with the computer system 36 may, for example, be a TCP/IP connection over a network. In the case of the expression database agent 31, the intelligence sub-process 24 (FIG. 2) thus encapsulates the remote host interface 37.

A laboratory expression agent 32 obtains gene sequence data from a laboratory system 40. The laboratory system 40 is another computer system that includes a host 40-1 and an expression database 40-2. However, the particular data of interest in the expression database 40-2 is obtained from a gene expression reader 40-3. The gene expression reader 40-3 is a laboratory instrument which process physical tissue samples to determine partial gene sequence information in the form of gene fragments, or gene expressions. These gene expressions are stored in the expression database 36-2.

The laboratory expression agent 32 uses a sensor process 22 that determines when a new expression record is added to the expression database 40-2. When such new data exists, the laboratory expression agent 32 invokes its intelligence process 24 to retrieve the data from the expression database 40-2. An effector process 26 then creates the appropriate sequence entry 16 and results entry 18 in the sequence database 12.

Figure 4:
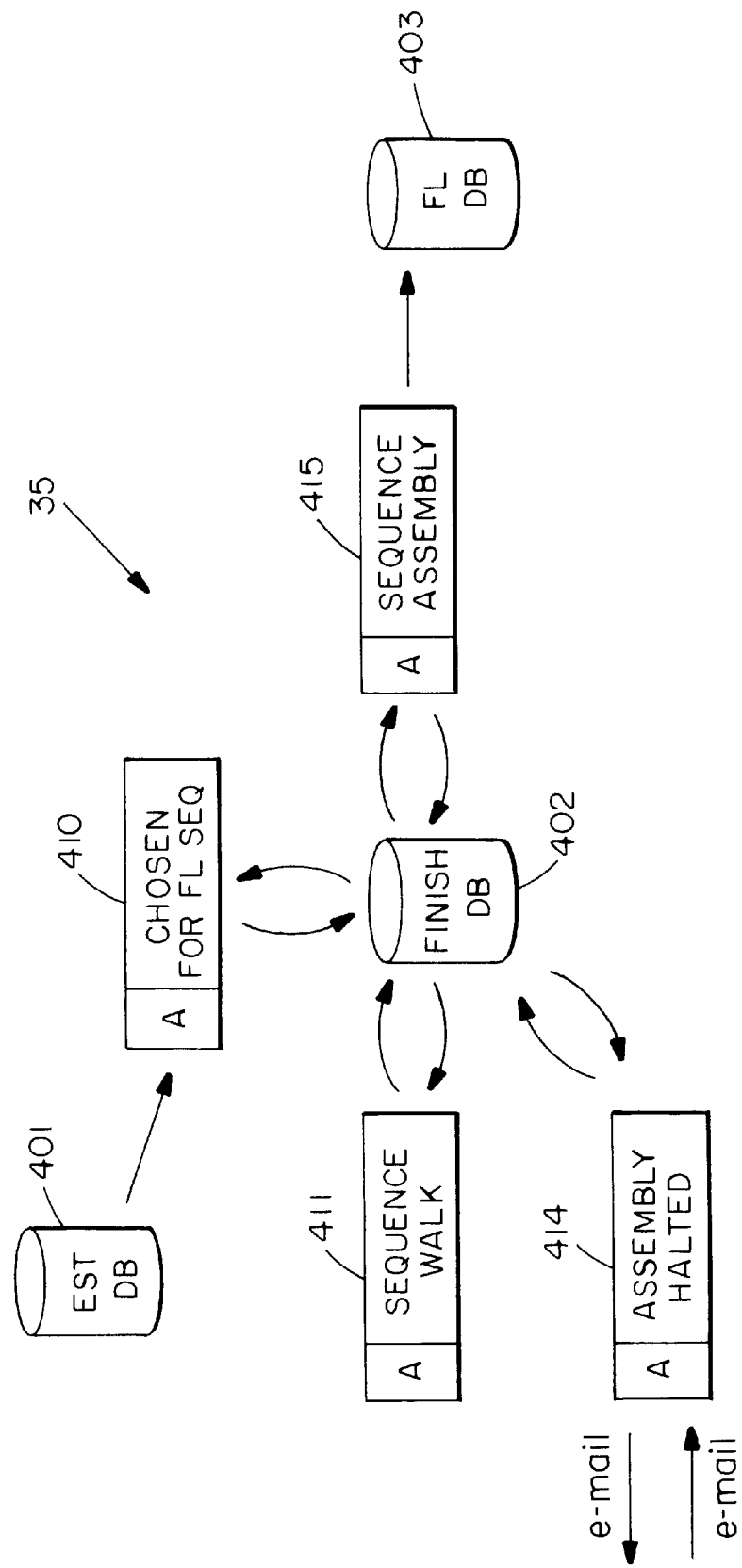
FIG. 4 is a symbolic diagram of a set of sequence finishing agents.

The laboratory system 40 operates autonomously from the gene sequence system 10, and gene sequence data resulting from tissue sample analysis may be placed in the expression database 40-2 at any time. It is only when the laboratory expression agent 32 is invoked as a process on the central processing unit 14, that the data is sought from the expression database 40-2 and then forwarded to the sequence database 12 in proper form. It is thus possible to have clones being subjected to analysis by the laboratory system 40, completely outside of other processes that are analyzing these same clones as implemented by the agents 20 running in the annotated database system 10. As described below in connection with FIG. 4, sequence finishing agents may be running at the same time that the laboratory system 40 is running.

A mathematical modeling agent 33 is typically responsible for reading sequence entries 16 and performing various mathematical algorithms on them. This may, for example, be a structure analysis algorithm that analyzes gene sequence data for the existence of secretory proteins. As shown, the code which implements the algorithm may typically reside as part of the intelligence process 24. Alternatively, the secondary structure code may exist and run on a separate piece of hardware, in which case the intelligence process 24 might typically include an appropriate Application Programmer Interface (API) software for accessing such code. The secondary structure code typically returns a score based upon a mathematical analysis of the gene sequence under examination. This core then becomes the data recorded in the annotation entry 18 by the effector process 24.

A comparison agent 34 is responsible for comparing one or more gene sequence entries 16 against other gene sequence entries 16 to find a degree of match between them. The particular comparison agent process 34 described here makes use of external super-computer hardware in order to perform such comparisons. For example, the supercomputer may include a Fast Data Finder (FDF) that makes use of a Smith/Waterman algorithm such as is available from Paracel Corporation. The comparison agents 34 communicates with the Fast Data Finder hardware 43 such as over a local area network (LAN) interface 42.

Figure 3A:
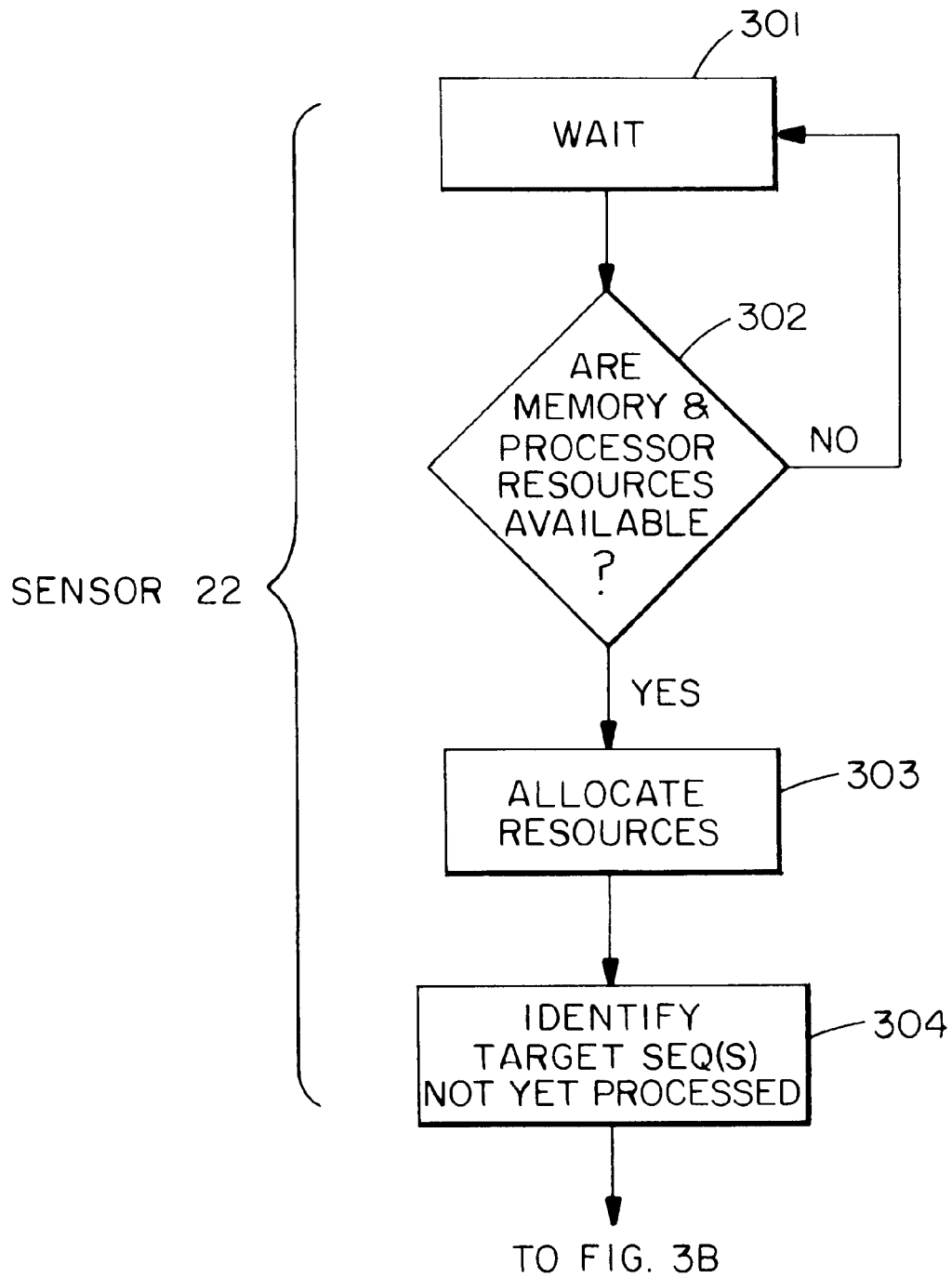
FIGS. 3A through 3C are flow diagrams for a specific comparison agent process that includes a sensor sub-process, intelligence sub-process, and effector sub-process, respectively.
Figure 3B:
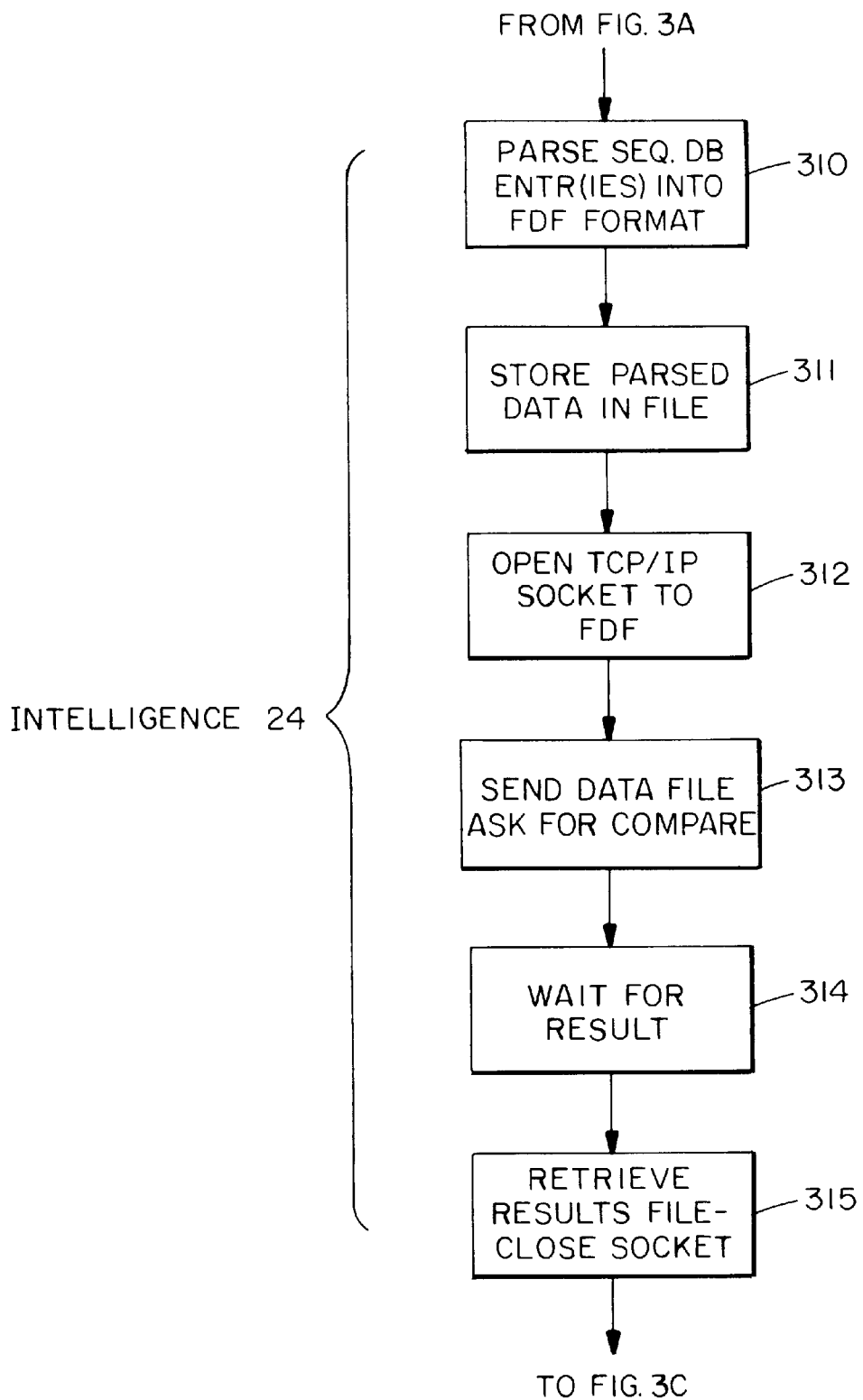
Figure 3C:
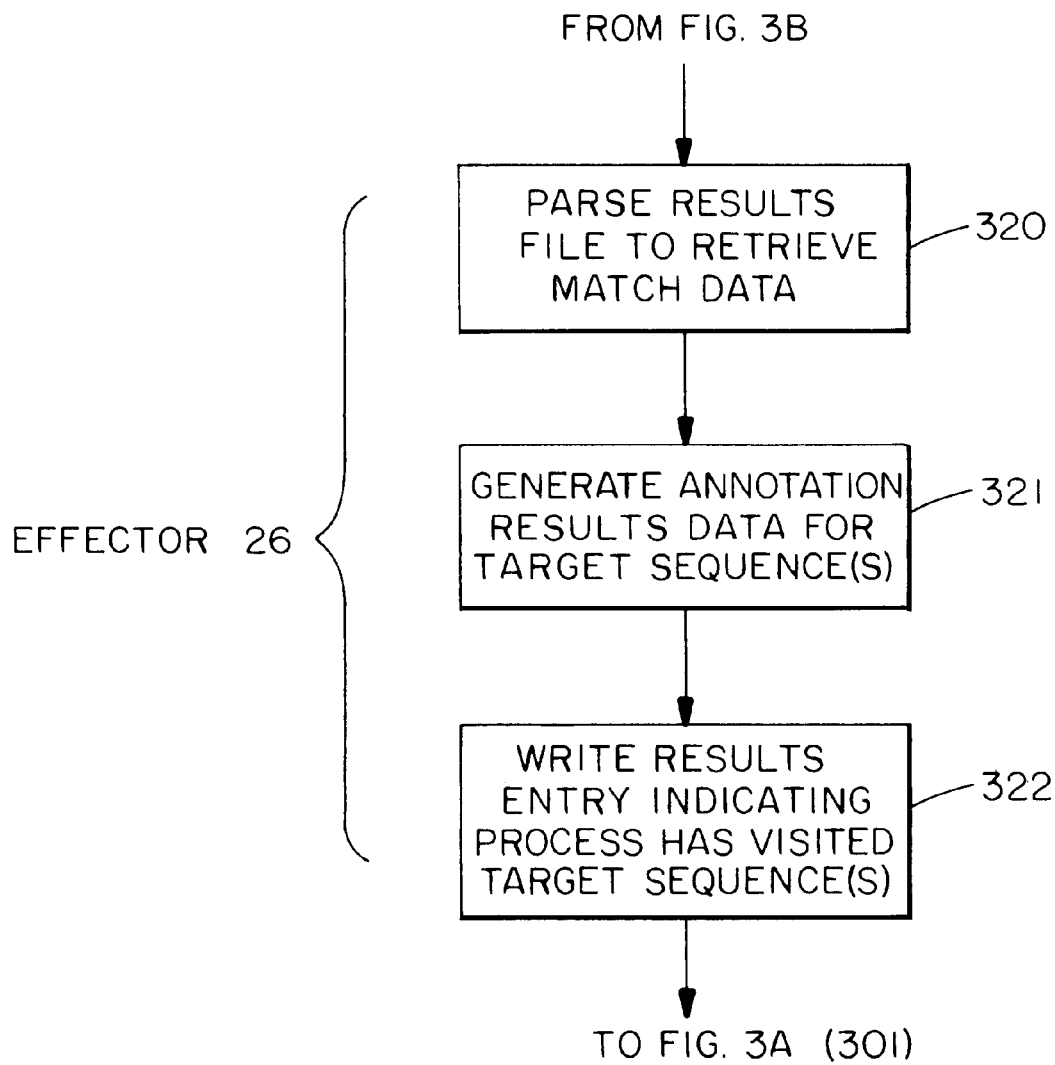

FIGS. 3A through 3C are a more detailed set of flow diagrams for one implementation of the comparison agent 34. FIG. 3A is a state diagram of the sensor sub-process 22, FIG. 3B is a detailed state diagram of the intelligence sub-process, and FIG. 3C is a state diagram of the effector sub-process 26.

As shown in an initial state 301, the comparison agent 34 is in a wait state in which it remains quiescent. The wait state 301 is an example, in an object oriented implementation of the comparison agent 34, of a component which may use the generic agent core 30.

From state 301, the comparison agent process 34 periodically enters a state 302. In this state 302, the sensor sub-process 22 determines whether sufficient processor resources such as memory, available processor time, local area network access ports, and other resources necessary for executing the remainder of the comparison agent process 34 are available. If this is not the case then the sensor process 22 returns to state 301. If, however, sufficient resources are available, then the sensor sub-process 22 continues to state 302.

State 302 is an example of a state which may take advantage of both the agent core 30 as well as code specific to the particular agent 20. In this case, the code necessary for determining whether sufficient memory and central processing unit resources are available may be part of the agent core 30. However, in the specific instantiation of sensor process 22 for the comparison agent 34, the portion of state 302 which determines whether sufficient local area network access ports are available may be solely implemented for in comparison agent 34.

From state 302, the sensor sub-process 22 continues to a state 303. In this state 303, the resources necessary for continuing the comparison agent process 34 are allocated. Processing then continues to a state 304 in which target sequence entries 16 not yet processed by the comparison agent 34 are identified.

In FIG. 3B the intelligence sub-process 24 is shown in more detail. In a first state 310, the sequence entries 16 identified to the intelligence sub-process 24 are placed in proper format for communication to the Fast Data Finder hardware. In a next state 311, the parsed data is stored in a data file. In a following state 312, a communication connection such as in the form of a TCP/IP socket is opened to the Fast Data Finder hardware.

Processing continues to a state 313 where the data file is sent over the TCP/IP connection, and the Fast Data Finder hardware is asked to initiate a comparison operation. In state 314 the intelligence sub-process 24 waits for a result. In a final state 315, the intelligence sub-process 24 retrieves the results in the form of a data file from the Fast Data Finder hardware and closes the socket.

The comparison agent 34 then performs the effector sub-process 26 as shown in FIG. 3C. In a first state 320, the results file is parsed to retrieve match data of interest. In a next state 321, a results entry 18 is created for recording the results of the operation. This results entry 18 contains its own identification record 18-1, the sequence identification record 18-2, the agent identification record 18-3 associated with the comparison process 43, and a result record 18-4. In this case, the match data retrieved in state 320 is also written into the result data record 18-4. In state 322, the effector sub-process 26 also adds a record to the results entry 18 such as another result data record 18-4 that indicates that the comparison process 34 has visited the particular target sequence identified by sequence identification record 18-2.

This is the final state of the comparison process 34, and at this point, processing returns to state 301 of FIG. 3A in which the comparison-agent 34 is again available for processing other data.

By creating the annotation entry in state 322, which specifically indicates that the comparison process 34 has visited a particular target sequence 16, a mechanism therefore exists for tracking which data has been operated on by which version of each particular process. That is, it should be understood that the results entry 18 created in state 322 is preferably a different entry for each version of a sequence comparison process 34 that is running in the system 10. This serves two purposes. First, if the agent processes 20 fail to complete their tasks, the sequence database 12 is still intact. That is, by not indicating that a process has visited the target sequence until the data is actually completed for processing, then the particular sequence record 16 is again a candidate for processing when the comparison agent process 34 comes back online.

As mentioned briefly in connection with FIG. 2, a set of agents may also be used to accomplish a series of gene sequences related tasks using the system 10. As shown in more detail in FIG. 4, a set of sequence finishing agents 35, implements a sequence finishing process on the gene expression entries 16. The sequence finishing agent set 35 consists of a number of databases including an expressed sequence tag (EST) database 401, a finish database 402, and a full length sequence database 403.

The sequence finishing agent set 35 also consists of a number of agents including a chosen-for-finishing agent 410, a sequence walk agent 411, an assembly halted agent 414, and a sequence assembly agent 415.

The purpose of the sequence finishing agent set 35 is to assemble short gene fragments, such as may be available in the express sequence tag database 401, to assemble such gene fragments into complete full length gene sequences, and then to store assembled full length sequences in the full length data base 403. The sequence finishing process is required in genetic research since most laboratory equipment may obtain only approximately 500 elements of a gene sequence during any one operation, whereas the average length of a gene sequence is typically is excess of 3,000 elements.

The various databases associated with the sequence finishing agent set 35 may each be implemented as portions of the sequence database 12. In particular, the express sequence tag database 401 is actually a portion of the sequence database 12 consisting of sequence entries 16 that are in the form of expressed sequence tags. The finish database 402 is an intermediate database that has results entries 18 that are used to keep track of the state of the sequence finishing process. The full length database 403 contains sequence entries 16 that are the desired full length gene sequences.

Each of the sub-processes in the sequence finishing agent set 35 may be implemented as agent processes 20 as previously described above. For example, the chosen for finishing process 410 is the first agent to operate on the expressed sequence tag database 401. The chosen-for-finishing agent 410 searches through the express sequence tag database 401 for gene fragments of interest. Once a gene fragment of interest is found, then it is placed into the finish database 402 by the effector sub-process 26 in the chosen-for-finishing process 410. A results record containing an annotation indicating that the chosen-for-finishing process 410 has operated on the sequence entry 16 is then created.

The sequence walk agent 411 has a sensor sub-process 22 that ensures that elements necessary in order to assemble a sequence from gene fragments are available. This agent 411 thus has a sensor process 22 which looks for expressed sequence tags placed in the finish database 402 by the chosen-for-finishing process 410. The effector sub-process 24 of the sequence walk agent 411 uses known mathematical and other processing techniques to create a results entry 18 in the finish database 402, as part of its effector process 26, that contains data required so that expressed sequence tags may be assembled together in the proper order.

The assembly halted agent 414 may be used to search the finish database 402 for annotations in the results entries 18 that indicate sequence assembly has been halted. The effector process 26 in this agent may then alert a human process technician, such as by sending an e-mail message, that action is needed to attend to the halted assembly. The assembly halted agent 414 may perform other tasks, such as recording an annotation from a technician that the halt is now cleared, in order to create an annotation in the finish database 402 to that effect.

The sequence assembly agent 415 then completes the assembly of the gene fragments into a full length sequence. The sequence assembly agent 415 thus has a sensor process 22 which obtains annotations relating to how to create complete sequences from the finish database 402, and places these completed sequences in the full length database 404.

Figure 5:
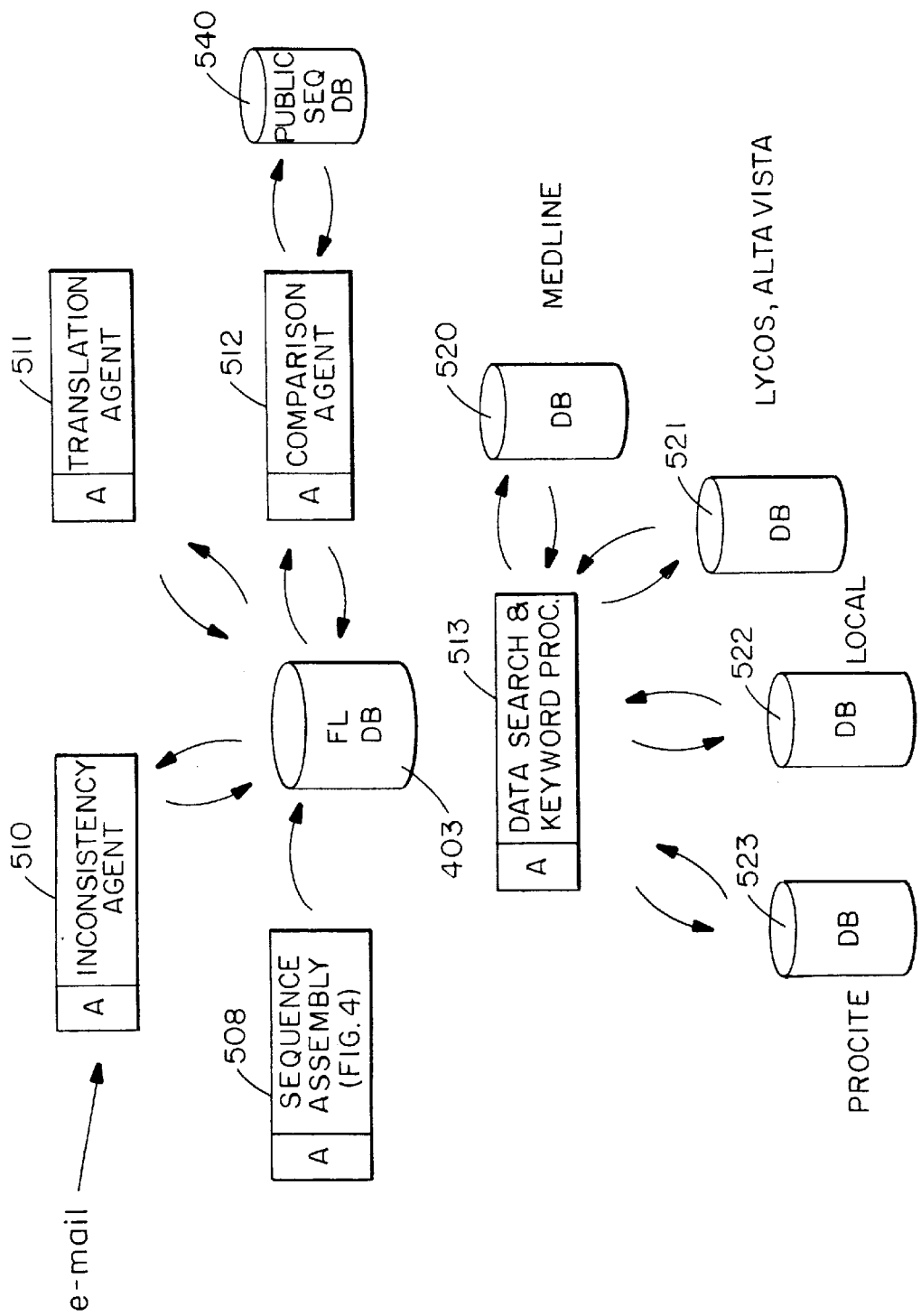
FIG. 5 is a symbolic diagram of a set of annotation agents.

FIG. 5 is a illustration of another example of the use of a set of agents 20 to accomplish a particular task. In this illustration, the agents 20 are used to implement a set of annotation functions associated with the full length database 403. In particular, these include a sequence locate agent 508, an inconsistency agent 510, a translation agent 511, a comparison agent 512, and a key word processing agent 513. The purpose of the various agents illustrated in FIG. 5 is to perform a set of operations that create annotations in the form of result records 18 that contain various types of information with respect to the full length sequences stored in the database 403.

For example, a sequence locate agent 508 may perform an initial search for gene sequences in need of annotation This sequence locate agent 508 may, for example, seek out full length sequences in the database 403 generated by the sequence finishing agent set 35.

An inconsistency agent 510 may then obtain information from an external source such as an e-mail system which creates results records 18 in the full length database 403 indicating the annotations made by human technicians. For example, the particular inconsistency agent 510 receives e-mail messages from the technicians indicating that, for example, a particular sequence did not assemble properly.

A translation agent 511 may be used to convert DNA type sequence information contained in the full length database 403 to other forms such as a predicted protein sequence. The results of the conversion are then stored as results records 18 as for the other agents described above.

A sequence comparison agent 512 may be tasked with searching through the full length database 403 to find sequences related to the particular sequences assembled by the sequence locating agent 508. In particular, information as to sequence analogues that may be available in public sequence databases 540. The comparison agent 512 is thus a particular instance of the agent 34 previously described in connection with FIG. 1.

Finally, the key word processing agent 513 in one example of an agent which obtains annotation information for the full length sequences from various external databases. These databases, may for example, include access to public resources such as the MedLine database 520, Internet search engines 521 such as Lycos or Alta Vista, a local information database 522 produced by the laboratory, or other information such as may be available from a public database such as ProSite.

While this invention has been particularly shown and described with references to the preferred embodiments thereof, it will be understood by those of skill in the art that various changes in form and details may be made therein without departing from the spirit and scope of the invention as defined by the appended claims.

What is claimed is:

1. A genetic database system comprising:

a database of gene sequence entries, the gene sequence entries containing gene sequence data;

a plurality of programs for processing the gene sequence data;

a database of results entries containing results records generated by the application of the programs to the gene sequence entries;

a plurality of autonomous agent programs, each agent program comprising:
(A) a sensor process that seeks target gene sequence data to be processed by at least one of the programs;
(B) an intelligence process that invokes the at least one program to process the target gene sequence data; and
(C) an effector process for revising the results records in response to the intelligence process.

2. A database system as in claim 1 wherein each autonomous agent records annotations in the results records in accordance with output produced by at least one program.

3. A database system as in claim 1 wherein each autonomous agent includes a sensor process that determines the availability of system resources.

4. A database system as in claim 1 wherein the sensor process additionally invokes the intelligence process.

5. A database system as in claim 1 wherein the effector process calls a sensor process for processing other target gene sequence data.

6. A database system as in claim 1 wherein the agents run as self-invoking processes in a multitasking data processing environment.

7. A database system as in claim 1 wherein the agents include an effector process which revises the results entries with a gene sequence annotation record.

8. A database system as in claim 1 wherein the results records include a flag record indicating that a particular version of the program has processed at least one of the gene sequence entries.

9. A database system as in claim 1 wherein the results record contains output produced by at least one program.

10. A database system as in claim 1 wherein the agents are implemented as object oriented programs.

11. A database system as in claim 1 wherein the sensor process selects a candidate gene sequence entry for processing by the agent.

12. A database system as in claim 1 wherein the results records comprise a sequence identification record that uniquely identifies the program which created the results entry.

13. A database system as in claim 1 wherein a least one of the agents is an expression database agent having an intelligence process that obtains gene expression data from an expression database external to the database of gene sequence records.

14. A database system as in claim 1 wherein at least one of the agents is a laboratory expression agent having an intelligence process that obtains gene expression data from a laboratory analyzer.

15. A database system as in claim 1 wherein the intelligence process compares gene sequence records.

16. A database system as in claim 1 wherein at least one of the agents is a sequence assembly agent.

17. A database system as in claim 16 wherein a group of the sequence entries comprise an expressed tag sequence database of partial gene sequences, and the sequence assembly agent is a set of agents comprising a chosen-for-finishing agent having an intelligence process which identifies expressed sequence tags that are in need of assembly.

18. A database system as in claim 17 wherein a group of the sequence entries comprise a finish database.

19. A database system as in claim 18 wherein the chosen-for-finishing agent includes an effector process that adds a results entry to indicate the sequence entry in the finish database is in need of sequence assembly.

20. A database system as in claim 18 wherein the sequence finishing agent includes a sequence walk agent which adds a results entry to indicate instructions for finishing assembly of a sequence entry in the finish database.

21. A database system as in claim 18 wherein a group of sequence entries comprise a full length sequence database and the sequence finishing agent includes a sequence assembly agent that creates a sequence entry in the full length sequence database from data in the finish database.

22. A method of storing data in a genetic database system comprising the steps of:
storing a database of gene sequence entries, the gene sequence entries containing gene sequence data;
storing a plurality of programs using the gene sequence data as input;
storing a database of results entries containing results data records generated by the running the programs with the gene sequence entries as input; and
executing a plurality of autonomous agent programs, each autonomous agent program comprising the steps of:
(A) invoking a sensor process that seeks target gene sequence data to be processed by at least one of the stored programs;
(B) invoking an intelligence process that applies at least one program to process the target data; and
(C) invoking an effector process for revising the results entries in response to invoking the intelligence process.

23. A method as in claim 22 wherein the step of invoking an effector process comprises a step of creating annotation entries in accordance with output produced by at least one program.

24. A database system as in claim 22 wherein the step of invoking a sensor process comprises a step of determining the availability of system resources.

25. A database system as in claim 22 wherein the step of invoking a sensor process comprises a step of autonomously invoking the intelligence process.

26. A database system as in claim 22 wherein the step of invoking an effector process comprises a step of autonomously invoking a sensor process for processing other target gene sequence data.

27. A method as in claim 22 wherein the step of executing the plurality of autonomous agent programs comprises a set of steps of executing self-invoking processes in a multitasking data processing environment.

28. A method as in claim 22 wherein the step of executing the plurality of autonomous agent programs comprises the step of invoking an effector process which revises the results records with annotation data.

29. A method as in claim 28 wherein the step of invoking an effector process comprises revising the results records with a flag record indicating that a particular version of the program has annotated at least one of the gene sequence entries.

30. A method as in claim 28 wherein the step of invoking an effector process comprises revising the results records with output data produced by the program.

31. A method as in claim 22 wherein the step of executing agent programs comprises executing agent programs that are implemented as object oriented programs.

32. A method as in claim 22 wherein the step of invoking a sensor process additionally includes the step of selecting a candidate gene sequence entry for processing by the autonomous agent program.

33. A method as in claim 22 wherein the step of invoking an effector process comprises the step of revising the results records to contain a sequence identification record that uniquely identifies the program which created the results entry.

34. A method as in claim 22 wherein a least one of the autonomous agents is an expression database agent and the step of invoking an intelligence process comprises the step of obtaining gene expression data from an expression database external to the database of gene sequence records.

35. A database system as in claim 22 wherein at least one of the agents is a laboratory expression agent and the step of invoking an intelligence process comprises obtaining gene expression data from by a laboratory analyzer.

36. A method as in claim 22 wherein the step of invoking an intelligence process comprises the step of comparing gene sequence records.

37. A method as in claim 22 wherein the step of executing a plurality of autonomous agent programs executes a sequence assembly agent program.

38. A method as in claim 37 wherein a group of the sequence entries comprise an expressed tag sequence database of partial gene sequences, and the step of executing a sequence assembly agent includes a step of executing a chosen-for-finishing agent which invokes an intelligence process which identifies expressed sequence tags that are in need of assembly.

39. A method as in claim 38 wherein the step of storing a database of gene sequence entries comprises a step of storing gene sequence entries comprising a finish database.

40. A method as in claim 39 wherein the step of executing a chosen-for-finishing agent additionally comprises the step of invoking an effector process that adds an annotation entry to the result record to indicate the sequence entry in the finish database is in need of sequence assembly.

41. A method as in claim 39 wherein the step of executing a sequence assembly agent additionally comprises the step of invoking a sequence walk agent adds a results entry to indicate instructions for finishing assembly of a sequence entry in the finish database.

42. A database system as in claim 39 wherein a group of sequence entries comprise a full length sequence database and the step of executing a sequence assembly agent comprises creating a sequence entry in the full length sequence database from data in the finish database.

* * * * *